United States Patent [19]

Buergisser

[11] Patent Number: 4,992,366
[45] Date of Patent: Feb. 12, 1991

[54] PROCESS FOR PRODUCING A RECEPTOR PREPARATION FOR A RADIORECEPTOR ASSAY AND KIT-CORRECT RADIORECEPTOR ASSAY ACCORDING TO THE PROCESS

[75] Inventor: Ernst Buergisser, Wangen, Switzerland

[73] Assignee: Anawa Laboratorien AG, Wangen, Switzerland

[21] Appl. No.: 221,511

[22] PCT Filed: Sep. 24, 1987

[86] PCT No.: PCT/CH87/00122
§ 371 Date: Jun. 10, 1988
§ 102(e) Date: Jun. 10, 1988

[87] PCT Pub. No.: WO88/02861
PCT Pub. Date: Apr. 21, 1988

[30] Foreign Application Priority Data

Oct. 13, 1986 [CH] Switzerland ............... 4079/86-7

[51] Int. Cl.$^5$ .............................. C12Q 1/16
[52] U.S. Cl. .......................... 435/35; 435/1; 436/804; 436/808
[58] Field of Search ............ 435/1, 35; 436/804, 436/808

[56] References Cited

U.S. PATENT DOCUMENTS

| | | | |
|---|---|---|---|
| 4,162,003 | 7/1979 | Bartos et al. | 206/219 |
| 4,197,288 | 4/1980 | Snyder . | |
| 4,259,207 | 3/1981 | Fruitstone et al. | 252/408 |
| 4,461,829 | 7/1984 | Greenquist | 435/7 |

FOREIGN PATENT DOCUMENTS

86/02004 4/1986 World Int. Prop. O. .

OTHER PUBLICATIONS

Buregisser et al., Biochem., Biophys. Res. Comm., vol. 133, pp. 1202–1209, 1985.

Primary Examiner—Robert A. Wax
Assistant Examiner—Jeffrey Stucker
Attorney, Agent, or Firm—Walter C. Farley

[57] ABSTRACT

A receptor preparation of biologically active receptor material is produced in which a cell membrane preparation is lyophilized accompanied by the addition of sugars and/or amino acids and/or proteins. A radioreceptor assay can be produced therefrom, which contains the colyophilizate of cell membrane together with sugar compounds and/or amino acids and/or proteins, as well as a tracer substance and a comparison standard substance. A radioreceptor assay kit uses the radioreceptor assay by making available the substances in a plurality of test containers containing a colyophilizate suitable for the assay.

16 Claims, No Drawings

PROCESS FOR PRODUCING A RECEPTOR PREPARATION FOR A RADIORECEPTOR ASSAY AND KIT-CORRECT RADIORECEPTOR ASSAY ACCORDING TO THE PROCESS

The invention relates to the field of biochemical analytical methods and relates to a process for producing a stable receptor preparation for a stable (multicomponent) radioreceptor assay and to the radioreceptor assay obtained by this process, its kit and the use of said kit or said assay.

BACKGROUND OF THE INVENTION

In the same way as with a radioimmunoassay, the principle of the radioreceptor assay is based on the biospecific detection of a ligand (used in a planned manner for the assay), e.g. a hormone, pharmacon, neurotransmitter, etc. at the corresponding target or acceptor molecule, e.g. an antibody in the radioimmunoassay or a receptor in the radioreceptor assay. As a result of the radioactive labelling of such a ligand used in a planned manner, an observable molecule is obtained, i.e. the tracer, which is in competitive interaction with an unlabelled ligand and therefore the similar, but unobservable, molecule. Through such measures a test system is obtained, which makes it possible to measure an unknown concentration of such a ligand.

While radioimmunoassay has become a widely used routine method and is used to a significant extent as an analytical method at present, radioreceptor assay is only rarely used for this purpose.

One of the main reasons for this is that the handling of biologically active receptors is more difficult than with an antibody. The prerequisite for a routine method is, apart from relatively simple handling (method simplicity) and the accompanying economical aspects, mainly the "stability" of the chemical or biological reactant. This means the stability of the actual analysis substance and its stability within the analytical reaction.

However, in solution, biologically active receptors are unstable and must therefore be frozen solid until just before they undergo analytical use. In addition, they are so unstable that even if this condition is briefly not fulfilled, the receptor can be made unuseable. It is obvious that such sensitive characteristics make it impossible to use as a routine method such a fundamentally useable analysis mechanism.

SUMMARY OF THE INVENTION

The object of the invention is therefore to provide a way of supplying such sensitive substances to a simple routine method, which can be easily performed while being able to avoid the hitherto necessary measures such as freezing and the like with all the problems, disadvantages and risks associated therewith.

This objective is achieved through the preparation process for a radioreceptor assay and a radioreceptor assay produced by this process for direct analytical use.

DETAILED DESCRIPTION OF THE PREFERRED EMBODIMENT

The aim is that all or a maximum number of reactants can be present together in a common vessel and that the starting up of the bonding or binding reaction is performed with a single pipetting step, whereby apart from the material to be analysed, all the reaction participants are available in stable form, e.g. in a test tube. Conventional processes of this type generally require 3 to 4 pipetting stages, so that a considerable economic advance is provided in connection with such analytical methods made possible by the invention in a single process, (in connection with the speed of performing the test, the accuracy and the working expenditure). Moreover the invention leads to a test kit which, without quality loss, can be stored at ambient or refrigerator temperature (no freezing), which is particularly important in connection with transportation, because there is no need for the hitherto necessary dry ice for transportation purposes.

The process described hereinafter for the production of a stable radioreceptor assay leads to obtaining a dried, stable form.

The preparation of receptor-containing cell membranes is performed in accordance with methods described in the literature, e.g. according to E. Burgisser et al, Biochem. Biophys. Res. Commun., Vol.133, pp 1202–1209, 1985. This involves the obtaining of suitable tissue material or cells, e.g. blood cells or cell cultures. This is followed by cellular disintegration by homogenization, ultrasonics or some other suitable procedure, followed by separation of the cytoplasmatic (soluble) components, together with a separation of coarser particles, e.g. by centrifuging, filtering, etc. The resulting cell membrane preparation can now be used in a radioreceptor assay.

Up to now, this preparation has been prepared just prior to use in an assay, or has been deep frozen and stored up to the time of use in this state. This is where the inventive procedure differs from the prior art.

In place of deep freezing, the preparation is now lyophilized, i.e. freeze-dried. However, this step only leads to the desired objective, namely obtaining the biological activity of the receptors (the obtaining of the bonding capacity or power thereof) in a stable and less sensitive end product, which can be used after a random period of time, if suitable additives are added to the cell preparation. In itself, freeze-drying does not lead to a useable, biologically active analytical product.

These additives should have the following characteristics;

1. They must be chemically and biochemically inert, which means that they are not reactants of the test system and do not influence the same.
2. They must have a minimum or no hygroscopicity.
3. They must also be soluble in the solvents used for the assay, i.e., in the solvents used for dissolving the lyophilized product.
4. They should also ensure that the lyophilizate assumes a more voluminous and compact form which, being directly lyophilized in this way in the test vessel, remains firmly connected to the vessel wall even under a great mechanical action (shaking when dispatched by post).

These substances are sugar compounds and their derivatives, preferably monosaccharides, such as mannitol, glucose, fructose and further aldoses and ketoses, as well as disaccharides, such as lactose, saccharose and weakly reactive amino acids, such as glycine, etc. and/or additional albumins, preferably bovine serum albumin, together with soluble polysaccharides and collogens, e.g. gelatin.

EXAMPLE 1:

An aqueous solution suitable for the lyophilization of cell membranes comprises e.g.

| | |
|---|---|
| tris-buffer | 50 mM, pH 7.6 |
| bovine serum albumin | 0.5% |
| d-mannitol | 2% |
| stabilizers | proportion according to system |

The stabilizers to be used are mainly required in the liquid phase, which relates to the state of the preparation prior to lyophilization and during incubation in the analysis. In the case of substances with slight hygroscopicity, there is a risk of a premature, partial reaction and/or degeneration in the lyophilizate. The stabilizers are e.g. protease inhibitors, such as aprotinin (trasylol), leupeptin, etc., together with antioxidants, e.g. dithiothreitol (DTT), etc. and bacteriostatics, e.g. sodium azide, thimerosal and complexones, e.g. EDTA and EGTA. Their use is highly dependant on the particular assay system to be prepared and should be evaluated and optimised for each individual test system. The criteria for this correspond to the conventional stabilization of biologically active components, such as are used already in conventional processes.

EXAMPLE 2:

| | |
|---|---|
| phosphate buffer | 50 mM, pH 7.4 |
| human serum albumin | 0.2% |
| lactose | 5% |
| glycerol | 0.5 |
| sodium azide (stabilizer) | 0.01% |

EXAMPLE 3:

| | |
|---|---|
| HEPES buffer | 20 mM, pH 7.4 |
| gelatin | 1% |
| glycine | 2% |
| complexone III (EDTA) | 2 mM |

The following variant is derived from the above process. The simplification of the assay is based on the use of a single pipetting stage, e.g. the reaction of the lyophilizate in liquid reactive form. If a kit consists of several reactants, then by colyophilization these reaction participants can be incorporated. The dry mixture is then dissolved with the sample to be determined and consequently the reaction is started. Advantageously the composition is lyophilized in a test tube or cup of microtest plates in the correct quantity and composition.

In order to avoid an undesired preincubation during the preparation of the lyophilizate, the individual components can be sequentially introduced into the reaction vessel, which takes place e.g. in the following way. Each component reactive in the assay is sequentially deep-frozen in the test container in order to avoid thorough mixing in the liquid phase. Advantageously there is a nonreactive separating layer between each two reactive components. Such separating layers e.g. consist of the solution or buffer substance described in Example 1. These additions take place directly in the test container to contain the aliquoted assay and made available to the user for direct use. The following lyophilization naturally also takes place in this test container, which is subsequently adequately packed.

Such a mixture prepared for colyophilization consists of the following parts:

EXAMPLE 4 (COLYOPHILIZATE QUALITATIVE):

plasma cell preparation
tracer substance
possibly a standard
possibly stabilizers and/or modulators
possibly dyes for the visual differentiation of tests prepared in different ways
lyophilization medium according to Examples 1 or 2.

The modulators influence the bonding characteristics of ligands to the receptors, so that the adequate substances are chosen for each assay. Thus, e.g. the substance amiloride improves the bonding affinity of ANF to the plasma cell receptor from bovine adrenal cortex (Lit. A. DeLean, Lif.sei. 39,1109–1116,1986).

EXAMPLE 5(COLYOPHILIZATE QUANTITATIVE):

plasma cell from bovine adrenal cortex 10 mg/test biological starting material.
tracer: iodine 125-labelled ANF, ANP (Atrial Natriuretic Factor, Peptide): 20,000 cpm.
standard ANF (dilution series, only in one part of the test kit, e.g. 16 of 96 cups of a microtest plate).
phenanthroline (stabilizer): 1 mM
dye for labelling the standard series: Evans
Blue (concentration according to desired intensity).

The individual components are preferably dissolved in the lyophilization medium (50 mM tris-buffer, pH 7.6, 0.5% BSA, 2% mannitol) and sequentially frozen in the manner described above.

The lyophilization is performed in accordance with known processes, while ensuring that the frozen components cannot even briefly liquify, such that the lyophilization is complete and no residual moisture is left behind and that the test containers, test tubes, or microtest plates are sealed against moisture access immediately on removal from the lyophilizer and preferably the test container is filled with a dry inert gas, e.g. nitrogen or argon.

A radioreceptor assay prepared according to the inventive process is characterized by the following basic composition. The receptor-containing cell membrane preparation is present in lyophilized form, the previously added carrier substances (additives) ensuring that the dry mixture immediately changes into a homogenous solution following reconstitution in the assay buffer and without any mechanical action (stirring, etc). The lyophilizate is characterized by a relatively voluminous material, which can be recognized by the expert as a typical lyophilizate.

The lyophilized membrane preparation can be present both as the sole reactant or as a co-lyophilizate with other reactants. In an assay kit, the lyophilized membrane preparation can either be in a single vessel or already allocated in the test containers.

The present process is not only suitable for performing tests in tubes, but is also ideally suitable for the use of microtest plates which permits a high degree of automation.

A commercially available assay kit e.g. comprises one or more microtest plates of in each case 96 assays, which are sealed by means of suitable adhesive films against the penetration of moisture. As a result of the geometry of the microtest plates (flat articles), such a kit can be dispatched without difficulty by letter post. There is also no need for the hitherto required complicated and expensive dispatch procedure using coolants (dry ice).

I claim:

1. A process for producing a unit suitable for conducting a micro-scale radioreceptor assay, comprising the steps of
   (a) preparing separate solutions of:
      (i) a plasma membrane preparation containing receptors,
      (ii) a labeled ligand substance capable of interacting with said receptors, and
      (iii) a protective substance selected from the group consisting of sugars, amino acids, proteins, and combinations thereof;
   (b) adding one of solution a)i), a)ii) or a)iii) to a receptacle and shock freezing said solution; adding one of the remaining solutions and shock freezing said solution; and adding the remaining solution and shock freezing said solution;
   (c) lyophilizing said solutions; and
   (d) sealing the resultant lyophilizations against the penetration of moisture in a receptacle suitable for conducting said assay.

2. A process of claim 1, wherein at least one of the solutions of step (a) contains a comparison substance.

3. A process of claim 1, wherein at least one of the solutions of step (a) contains a stabilizer.

4. A process of claim 3 wherein the stabilizer comprises phenanthroline.

5. A process of claim 1, wherein at least one of the solutions of step (a) contains at least one modulator.

6. A process of claim 1, wherein at least one of the solutions of step (a) contains a dye.

7. A process of claim 1, wherein the receptacle of step (c) is one of a series of tubes or cups comprising a microtest plate.

8. A process of claim 1 further comprising the steps of
   (1) preparing a first solution which contains the plasma membrane preparation and protective substances;
   (2) preparing a second solution which contains the labelled ligand-substance;
   (3) placing a small, exactly dosed quantity of one of the two solutions of step (1) or (2) into the receptacle and deep freezing said solution therein to form a deep frozen layer;
   (4) placing a small, exactly dosed quantity of the other one of the two solutions of step (1) or (2) and deep freezing said solution above the first deep-frozen layer in the receptacle;
   (5) lyophilizing the layer-structure thus obtained; and
   (6) sealing the receptacle against the penetration of moisture.

9. A process of claim 8, wherein a non-reactive separating layer is deep-frozen onto the first deep-frozen layer in the receptacle between steps (3) and (4).

10. A process of claim 9, wherein the non-reactive separating layer comprises a solvent of the first solution.

11. A process of claim 9, wherein the non-reactive layer comprises a buffer solution.

12. A process of claim 8, wherein a third solution, which contains a comparison substance, is deep-frozen onto the deep-frozen layer of step (4).

13. A process of claim 12, wherein a non-reactive separating layer is deep-frozen onto the deep-frozen layer of step (4) before the third solution is deep-frozen thereto.

14. A process of claim 12, wherein the third solution contains a dye.

15. A process of claim 8, wherein the solution of step (1) comprises an aqueous mixture of plasma membrane preparation with 0.1 to 10% wt/vol of mannitol and/or 0.1 to 10% wt/vol of humane or bovine serum albinum.

16. A process of claim 8, wherein the solution of step (1) comprises an aqueous mixture of plasma membrane preparation with 0.1 to 10% wt/vol glycine and/or 0.1 to 10% wt/vol human or bovine serum albinum.

* * * * *